United States Patent
Wan et al.

(10) Patent No.: US 12,351,548 B2
(45) Date of Patent: Jul. 8, 2025

(54) METHOD FOR PREPARING CARBONYL SULFONE

(71) Applicant: SOOCHOW UNIVERSITY, Suzhou (CN)

(72) Inventors: Xiaobing Wan, Suzhou (CN); Hanghang Wang, Suzhou (CN); Yonggao Zheng, Suzhou (CN); Pengcheng Lian, Suzhou (CN); Jingjing Li, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 658 days.

(21) Appl. No.: 17/780,699

(22) PCT Filed: Nov. 27, 2020

(86) PCT No.: PCT/CN2020/132490
§ 371 (c)(1),
(2) Date: May 27, 2022

(87) PCT Pub. No.: WO2021/104503
PCT Pub. Date: Jun. 3, 2021

(65) Prior Publication Data
US 2023/0054928 A1  Feb. 23, 2023

(30) Foreign Application Priority Data
Nov. 29, 2019 (CN) .......................... 201911207676.7

(51) Int. Cl.
*C07C 315/02* (2006.01)
*C07C 315/06* (2006.01)

(52) U.S. Cl.
CPC .......... *C07C 315/02* (2013.01); *C07C 315/06* (2013.01); *C07C 2523/50* (2013.01)

(58) Field of Classification Search
USPC ......................................................... 568/28
See application file for complete search history.

(56) References Cited

U.S. PATENT DOCUMENTS 4,966,731 A   10/1990   Chou

FOREIGN PATENT DOCUMENTS

| CN | 104402782 A | 3/2015 |
|----|-------------|--------|
| CN | 108191718 A | 6/2018 |
| CN | 110818600 A | 2/2020 |
| DK | 0438994 T3  | 7/1995 |
| EP | 0008269 A1  | 2/1980 |

OTHER PUBLICATIONS

Yaxiong Wang et al., "Bu4NI-Catalyzed Cross-Coupling between Sulfonyl Hydrazides and Diazo Compounds to Construct !!Carbonyl Sulfones Using Molecular Oxygen" Org. Lett. 2016, 18, 5082-5085 (Sep. 20, 2016).

Hanghang Wang et al., "Cross coupling of sulfonyl radicals with silverbased carbenes: a simple approach to !-carbonyl arylsulfones" Org. Biomol. Chem., 2020, 18, 2163-2169 (Feb. 28, 2020).

*Primary Examiner* — Ana Z Muresan
(74) *Attorney, Agent, or Firm* — SZDC Law PC

(57) ABSTRACT

Disclosed is a method for preparing β-carbonyl sulfones. The method comprises: by taking an α-carbonyl diazo compound and sodium arylsulfinate as reaction substrates, cheap silver nitrate as an optimal catalyst, 1,10-phenanthroline as a ligand, and potassium persulfate as an oxidant, carrying out coupling reaction in a mixed solvent of acetonitrile and water to obtain a β-carbonyl sulfones compound. Compared with the prior art, the method has the following advantages: a wide range of reaction substrates, short reaction time, a relatively high reaction yield, a mild reaction condition, etc. In the present invention, non-toxic and harmless reagents are used as reaction raw materials, so that it has no harm to the environment and satisfies the requirements of contemporary green chemistry development. Post-reaction treatment is relatively simple, and is convenient for separation and purification. In addition, the reaction can achieve gram-scale synthesis, and lays a foundation for actual applications.

5 Claims, No Drawings

METHOD FOR PREPARING CARBONYL SULFONE

This application is the National Stage Application of PCT/CN2020/132490, filed on Nov. 27, 2020, which claims priority to Chinese Patent Application No. 201911207676.7, filed on Nov. 29, 2019, which is incorporated by reference for all purposes as if fully set forth herein.

TECHNICAL FIELD

The invention relates to a method for preparing β-carbonyl sulfones, which belongs to the technical field of organic synthesis.

BACKGROUND TECHNIQUE

Sulfone-based skeleton compounds are widely used. In organic synthetic chemistry, sulfone-based compounds are also an important reaction intermediate. Such as, using Julia alkenylation, Ramberg-Bäcklund reaction and Smiles rearrangement can be converted into corresponding target molecules. Because of their wide range of applications, they have received extensive attention from chemists in the past few decades. For this reason, a series of methods for synthesizing sulfone-based compounds have been developed. Among the numerous sulfone compounds, β-carbonyl sulfones compounds have been paid close attention. These compounds have wide range of activities and often used for the total synthesis of natural products and the synthesis of heterocyclic compounds. Therefore, the synthesis of β-carbonyl sulfones is of great importance in that. Through literature surveys, it is found that the current synthesis methods for β-carbonyl sulfones have some shortcomings more or less, such as harsh reaction conditions, poor atom economy, narrow substrate range, and cumbersome operation. For example:

(1) Karl Anker Jorgensen et al. reported that thiol compounds were reacted with α-bromocarbonyl compounds under alkaline conditions to obtain thioethers, and then oxidized with $H_5IO_6$ and a catalytic amount of $CrO_3$ to obtain the corresponding β-carbonyl groups. Sulfone compounds. However, a multi-step reaction was required and a large excess of oxidant was used (See K. A. Jorgensen. Eur. J. Org. Chem. 2011, 2011, 47).

(2) Knospe, R. H. et al. reported the use of Claisen condensation reaction strategy to achieve the synthesis of β-carbonyl sulfones, but the disadvantage was sodium ethoxide used in the reaction, which is not friendly to the environment, and the reaction steps were cumbersome and the substrate range was relatively narrow. (See Knospe, R H J Am. Chem. Soc. 1955, 77, 5063).

(3) ChenZhen-Chu used ketones and PhI(OH)OTs to reflux in acetonitrile solvent to obtain α-p-toluenesulfonyloxy substituted ketones, and then with sodium benzenesulfinate in a mixed solvent of acetonitrile and water Reflux to obtain the corresponding β-carbonyl sulfones compound. The disadvantage of the reaction is that the atomic economy of the reaction was relatively poor, the reaction conditions are relatively harsh, and the price of PhI(OH)OTs was relatively expensive.

In summary, the currently reported methods for synthesizing β-carbonyl sulfones have obvious shortcomings, such as high cost, cumbersome reaction operation, harsh reaction conditions, poor atom economy, and narrow substrate range. Therefore, it is particularly important to develop a method with rich sources of raw materials, high reactivity, low cost, safety, environmental protection, and simple operation to effectively synthesize β-carbonyl sulfones compounds.

TECHNICAL PROBLEM

The object of the present invention is to provide a method for preparing β-carbonyl sulfones which was distinguished by simple manipulation, easily available starting materials, and wide substrate scope.

TECHNICAL SOLUTIONS

In order to achieve the above-mentioned object of the invention, the technical solution adopted by the present invention is: a method for preparing a β-carbonyl sulfone, including: reacting an α-carbonyldiazo compound with a sodium arylsulfinate, an N,N-bidentate compound as a ligand, a peroxide as a oxidant, in the presence of a metal compound as a catalyst, in the mixed solvent of an organic solvent and water, to obtain the β-carbonyl sulfone.

This invention discloses an application of a metal compound as a catalyst in the reaction of an α-carbonyldiazo compound and a sodium arylsulfinate to prepare a β-carbonyl sulfone, the metal compound is a silver compound or a copper compound.

In the present invention, the α-carbonyldiazo compound has the following chemical formula:

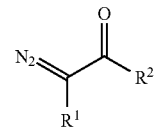

$R^1$ is selected from the group consisting of methyl, ethyl and hydrogen; $R^2$ is alkoxy; the sodium arylsulfinate has the following chemical formula:

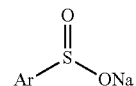

wherein, Ar is benzene or substituted benzene; the metal compound is a silver compound or a copper compound, preferably, silver nitrate; the peroxide is potassium persulfate, sodium persulfate or ammonium persulfate, preferably, potassium persulfate; the N,N-bidentate compound is 1,10-phenanthroline, 2,2'-bipyridine, 4,7-dimethoxy-1,10-phenanthroline, 4,7-diphenyl-1,10-phenanthroline, or 3,8-dibromo-1,10-phenanthroline, preferably, 1,10-phenanthroline.

The β-carbonyl sulfone has the following chemical formula:

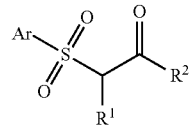

In the present invention, the reaction is conducted at 40 to 90° C., for 4 to 12 hours. Preferably, the reaction is conducted at 70° C., for 4 h.

In the present invention, a molar ratio of the catalyst to the sodium arylsulfinate is 1:10; a molar ratio of the oxidant to the sodium arylsulfinate is from 0.2:1 to 2:1, preferably, 0.5:1 and a molar ratio of the ligand to the sodium arylsulfinate is 10:1; a molar ratio of the α-carbonyldiazo compound to the sodium arylsulfinate is 2:1.

In the present invention, the reaction is conducted in the air.

In the present invention, the organic solvent is acetonitrile, preferably, the volume ratio of acetonitrile to water is 10:1.

The reaction is conducted in the air of the present invention. The reaction was then quenched with saturated $Na_2SO_3$ solution and the mixture was extracted with ethyl acetate. The organic layers were combined and dried with anhydrous $Na_2SO_4$. Removal of the organic solvent followed by flash column chromatographic purification using petroleum and ethyl acetate afforded the desired products.

BENEFICIAL EFFECTS

With the application of the above technical solutions, the present invention has the following advantages compared with the prior art:

1. The present invention preferably uses silver nitrate as the catalyst, 1,10-phenanthroline as the ligand, and 0.5 equivalent of potassium persulfate as the oxidant to realize the reaction of sodium benzenesulfinate and α-carbonyldiazo compound to prepare β-carbonyl sulfones. Compared with the cumbersome operation, harsh reaction conditions, and poor atom economy in the prior art, the reaction operation is simple, the atom economy is good, and the conditions are mild.

2. Compared with some existing technologies, the technology of the present invention does not need to be performed under strong alkaline conditions, and the reagents used are non-toxic and harmless, and are not harmful to the environment.

3. The invention adopts cheap catalysts, ligands and oxidants, and the reaction raw materials are cheap and easily available. The reaction steps are few, and a higher yield can be obtained in only one step, which meets the requirements of contemporary green chemistry development. For various alcohols, including alcohols with biological activity, diazonium compounds can be prepared, so as to achieve cross-coupling with sodium arylsulfinate to prepare corresponding β-carbonyl sulfones. Therefore, the substrate of the present invention is generally good adaptability.

EXAMPLES OF THE INVENTION

The following further describes the present invention with reference to the examples: reacting an α-carbonyldiazo compound with a sodium arylsulfinate, an N,N-bidentate compound as a ligand, a peroxide as an oxidant, in the presence of a metal compound as a catalyst, in the mixed solvent of an organic solvent and water, to obtain the β-carbonyl sulfone.

The catalyst, the oxidant, ligands, sodium benzenesulfinate, sodium 4-methylbenzene sulfinate, sodium 4-fluorobenzene sulfinate, sodium 4-chlorobenzene sulfinate and the organic solvent of the present invention are all commercialized products and can be purchased directly. Diazo compounds are prepared with corresponding alcohols or amines as starting materials according to their different structures Example 1

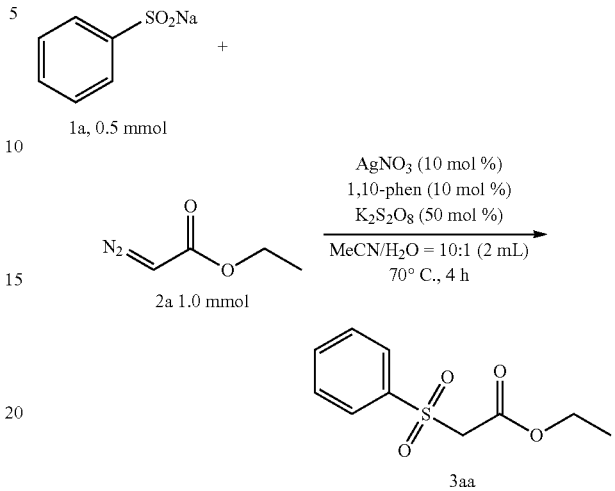

Compound $AgNO_3$ (0.05 mmol, 8.5 mg), 1,10-phen (0.05 mmol, 9.0 mg), $K_2S_2O_8$ (0.25 mmol, 67.6 mg), 1a (0.5 mmol, 82.1 mg), 2a (1.0 mmol, 114.1 mg), MeCN/$H_2O$=10:1 (2.0 mL). The reaction mixture was heated at 70° C. for 4 h, and the reaction was then quenched with saturated $Na_2SO_3$ solution and the mixture was extracted with ethyl acetate (20 mL×3). The organic layers were combined and dried with anhydrous $Na_2SO_4$. Removal of the organic solvent followed by flash column chromatographic purification using petroleum and ethyl acetate to obtain β-carbonyl sulfones 3aa, in a yield 80%. When the reaction was scaled up to 10 mmol (compound 1a), the yield of target product 3aa was still 74%. The analytical data of the prepared product are as follows. The data of the actual synthetic products are consistent with the theoretical analysis.

$^1$H NMR (400 MHz, $CDCl_3$) δ 7.97-7.95 (m, 2H), 7.72-7.68 (m, 1H), 7.61-7.57 (m, 2H), 4.17-4.12 (m, 4H), 1.19 (t, J=7.1 Hz, 3H). $^{13}$C NMR (100 MHz, $CDCl_3$) δ 162.2, 138.7, 134.2, 129.2, 128.5, 62.3, 61.0, 13.8. HRMS (ESI-TOF): Anal. Calcd. For $C_{10}H_{12}O_4S+Na^+$: 251.0349, Found: 251.0353. IR (neat, $cm^{-1}$): υ 3066, 2984, 2926, 2852, 1736, 1447, 1276, 1149.

Example 2

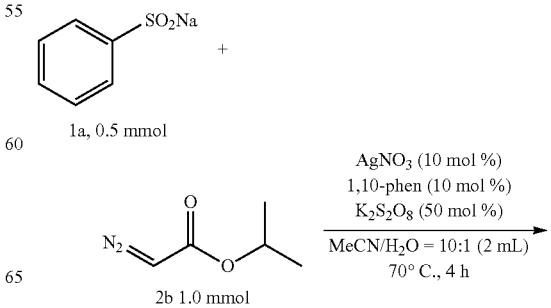

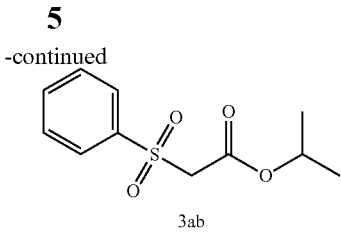

3ab

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2b (1.0 mmol, 128.1 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ab, in a yield 76%. The analytical data of the prepared product are as follows. The data of the actual synthetic products are consistent with the theoretical analysis.

¹H NMR (400 MHz, CDCl₃) δ 7.97-7.94 (m, 2H), 7.71-7.67 ((m, 1H), 7.60-7.57 (m, 2H), 4.99-4.93 (m, 1H), 4.12 (s, 2H), 1.15 (d, J=6.3 Hz, 6H). ¹³C NMR (100 MHz, CDCl₃) δ 161.6, 138.6, 134.1, 129.0, 128.3, 70.2, 61.0, 21.2. HRMS (ESI-TOF): Anal. Calcd. For $C_{11}H_{14}O_4S+Na^+$: 265.0505, Found: 265.0511. IR (neat, cm⁻¹): υ 3067, 2984, 2940, 2881, 1731, 1448, 1278, 1151.

Example 3

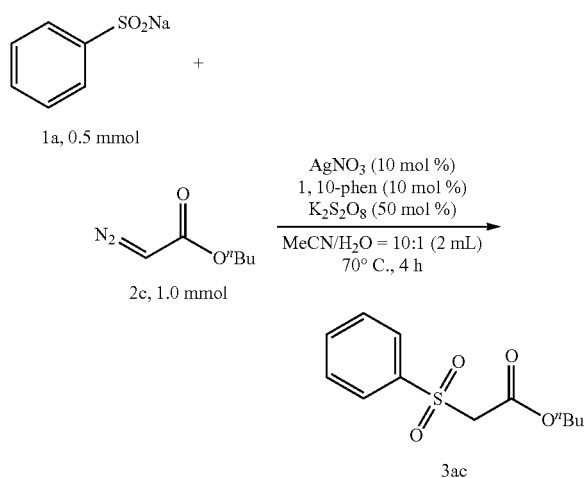

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2c (1.0 mmol, 142.2 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ac, in a yield 70%. The analytical data of the prepared product are as follows. The data of the actual synthetic products are consistent with the theoretical analysis.

¹H NMR (400 MHz, CDCl₃) δ 7.96-7.94 (m, 2H), 7.71-7.67 ((m, 1H), 7.60-7.56 (m, 2H), 4.15 (s, 2H), 4.07 (t, J=6.7 Hz, 2H), 1.55-1.48 (m, 2H), 1.31-1.22 (m, 2H), 0.87 (t, J=7.4 Hz, 3H). ¹³C NMR (100 MHz, CDCl₃) δ 162.2, 138.6, 134.1, 129.0, 128.2, 65.9, 60.7, 30.0, 18.6, 13.3. HRMS (ESI-TOF): Anal. Calcd. For $C_{12}H_{16}O_4S+Na^+$: 279.0662, Found: 279.0668. IR (neat, cm⁻¹): υ 2960, 2937, 2875, 1736, 1448, 1279, 1150, 1083.

Example 4

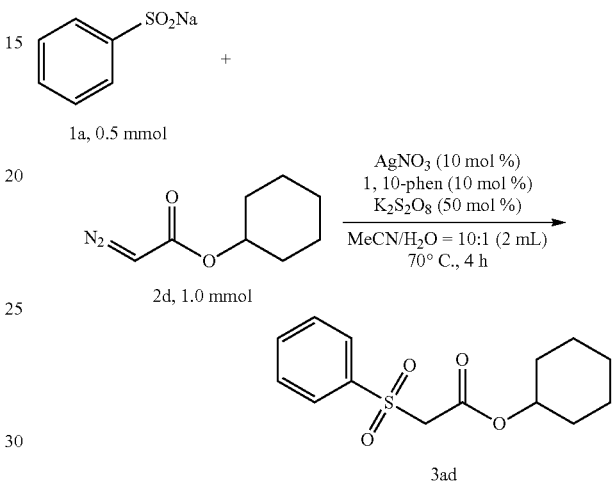

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2d (1.0 mmol, 168.2 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ad, in a yield 72%. The analytical data of the prepared product are as follows. The data of the actual synthetic products are consistent with the theoretical analysis.

¹H NMR (400 MHz, CDCl₃) δ 7.97-7.94 (m, 2H), 7.71-7.67 ((m, 1H), 7.60-7.56 (m, 2H), 4.76-4.57 (m, 1H), 4.12 (s, 2H), 1.77-1.64 (m, 4H), 1.53-1.48 (m, 1H), 1.37-1.18 (m, 5H). ¹³C NMR (100 MHz, CDCl₃) δ 161.7, 138.7, 134.1, 129.1, 128.4, 75.0, 61.1, 31.0, 25.0, 23.3. HRMS (ESI-TOF): Anal. Calcd. For $C_{14}H_{18}O_4S+Na^+$: 305.0818, Found: 305.0822. IR (neat, cm⁻¹): υ 3065, 2937, 2860, 1731, 1448, 1281, 1150, 1083.

Example 5

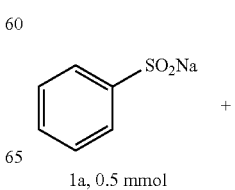

1a, 0.5 mmol

+

-continued

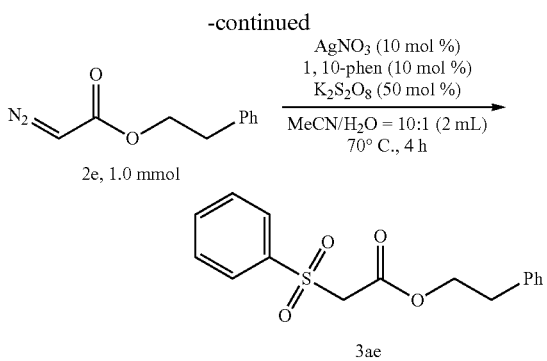

2e, 1.0 mmol

Compound AgNO$_3$ (0.05 mmol, 8.5 mg), 1,10-phen (0.05 mmol, 9.0 mg), K$_2$S$_2$O$_8$ (0.25 mmol, 67.6 mg), 1a (0.5 mmol, 82.1 mg), 2e (1.0 mmol, 190.2 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3ae, in a yield 87%. The analytical data of the prepared product are as follows. The data of the actual synthetic products are consistent with the theoretical analysis.

$^1$H NMR (400 MHz, CDCl$_3$) δ 7.89-7.87 (m, 2H), 7.65-7.61 (m, 1H), 7.53-7.49 (m, 2H), 7.28-7.24 (m, 2H), 7.22-7.18 (m, 1H), 7.13-7.11 (m, 2H), 4.25 (t, J=7.1 Hz, 2H), 4.09 (s, 2H), 2.82 (t, J=7.1 Hz, 2H). $^{13}$C NMR (100 MHz, CDCl$_3$) δ 162.1, 138.4, 136.8, 134.1, 129.0, 128.6, 128.3, 128.2, 126.5, 66.4, 60.6, 34.3. HRMS (ESI-TOF): Anal. Calcd. For C$_{16}$H$_{16}$O$_4$S+Na$^+$: 327.0662, Found: 327.0652. IR (neat, cm$^{-1}$): υ 3005, 2968, 2935, 1737, 1448, 1270, 1161, 1082.

Example 6

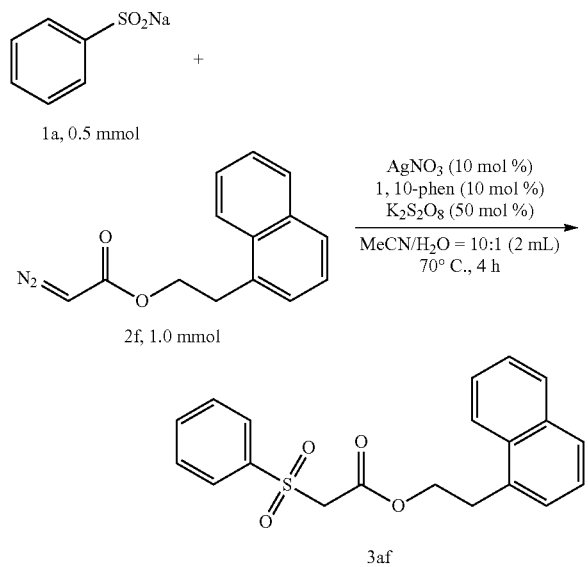

Compound AgNO$_3$ (0.05 mmol, 8.5 mg), 1,10-phen (0.05 mmol, 9.0 mg), K$_2$S$_2$O$_3$ (0.25 mmol, 67.6 mg), 1a (0.5 mmol, 82.1 mg), 2f (1.0 mmol, 240.3 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3af, in a yield 87%. The analytical data of the prepared product are as follows. The data of the actual synthetic products are consistent with the theoretical analysis.

$^1$H NMR (400 MHz, CDCl$_3$) δ 7.94 (d, J=8.0 Hz, 1H), 7.88-7.83 (m, 3H), 7.73 (d, J=8.0 Hz, 1H), 7.61-7.57 (m, 1H), 7.52-7.45 (m, 4H), 7.39-7.35 (m, 1H), 7.27-7.26 (m, 1H), 4.38 (t, J=7.3 Hz, 2H), 4.09 (s, 2H), 3.29 (t, J=7.3 Hz, 2H). $^{13}$C NMR (100 MHz, CDCl$_3$) δ 162.2, 138.5, 134.2, 133.7, 132.7, 131.7, 129.1, 128.8, 128.3, 127.5, 127.0, 126.2, 125.6, 125.4, 123.2, 66.0, 60.8, 31.6. HRMS (ESI-TOF): Anal. Calcd. For C$_{20}$H$_{18}$O$_4$S+Na$^+$: 377.0818, Found: 377.0817. IR (neat, cm$^{-1}$): υ 3060, 3005, 2968, 2935, 1733, 1448, 1270, 1160.

Example 7

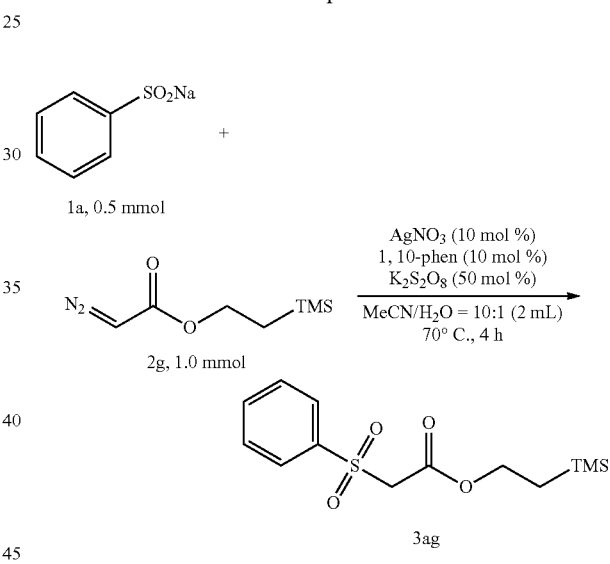

Compound AgNO$_3$ (0.05 mmol, 8.5 mg), 1,10-phen (0.05 mmol, 9.0 mg), K$_2$S$_2$O$_8$ (0.25 mmol, 67.6 mg), 1a (0.5 mmol, 82.1 mg), 2g (1.0 mmol, 186.3 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3ag, in a yield 72%. The analytical data of the prepared product are as follows. The data of the actual synthetic products are consistent with the theoretical analysis.

$^1$H NMR (400 MHz, CDCl$_3$) δ 7.97-7.94 (m, 2H), 7.69-7.67 ((m, 1H), 7.60-7.56 (m, 2H), 4.18-4.14 (m, 2H), 4.11 (s, 2H), 0.93-0.89 (m, 2H), 0.01 (s, 9H). $^{13}$C NMR (100 MHz, CDCl$_3$) δ 162.3, 138.7, 134.1, 129.1, 128.4, 64.7, 60.9, 17.0, −1.8. HRMS (ESI-TOF): Anal. Calcd. For C$_{13}$H$_{20}$O$_4$SSi+Na$^+$: 323.0744, Found: 323.0743. IR (neat, cm$^{-1}$): ν 3066, 2954, 2899, 1736, 1448, 1274, 1150, 1084.

Example 8

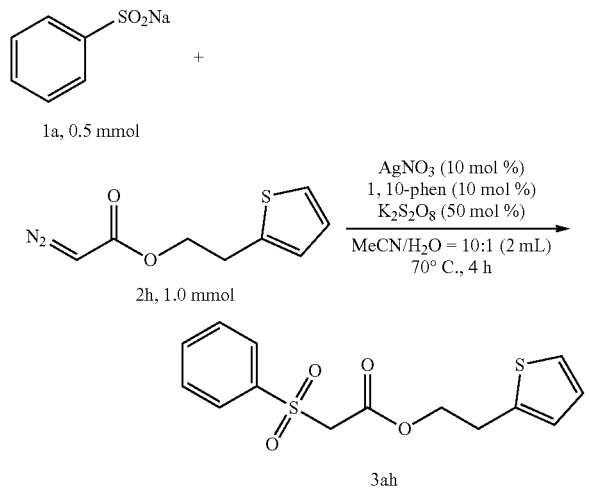

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2h (1.0 mmol, 196.2 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ah, in a yield 81%. The analytical data of the prepared product are as follows. The data of the actual synthetic products are consistent with the theoretical analysis.

$^1$H NMR (400 MHz, CDCl₃) δ 7.93-7.90 (m, 2H), 7.68-7.65 (m, 1H), 7.57-7.53 (m, 2H), 7.14-7.13 (m, 1H), 6.92-6.90 (m, 1H), 6.80-6.79 (m, 1H), 4.28 (t, J=6.8 Hz, 2H), 4.13 (s, 2H), 3.05 (t, J=6.8 Hz, 2H). $^{13}$C NMR (100 MHz, CDCl₃) δ 162.1, 138.8, 138.5, 134.2, 129.1, 128.3, 126.9, 125.6, 124.0, 66.1, 60.7, 28.6. HRMS (ESI-TOF): Anal. Calcd. For C₁₄H₁₄O₄S₂+Na⁺: 333.0226, Found: 333.0226. IR (neat, cm⁻¹): υ 3104, 3006, 2962, 2853, 1736, 1449, 1270, 1160.

Example 9

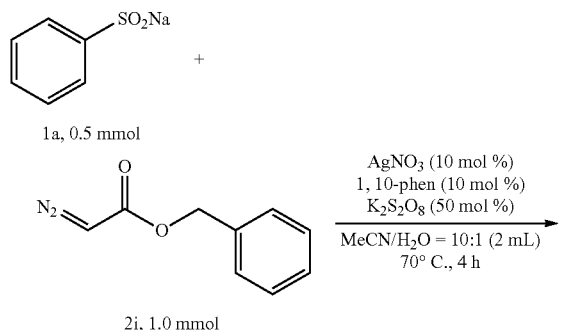

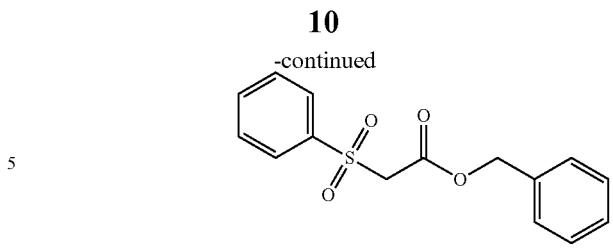

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2i (1.0 mmol, 176.2 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ai, in a yield 66%. The analytical data of the prepared product are as follows. The data of the actual synthetic products are consistent with the theoretical analysis.

$^1$H NMR (400 MHz, CDCl₃) δ 7.86-7.83 (m, 2H), 7.64-7.60 (m, 1H), 7.49-7.45 (m, 2H), 7.35-7.31 (m, 3H), 7.25-7.23 (m, 2H), 5.09 (s, 2H), 4.15 (s, 2H). $^{13}$C NMR (100 MHz, CDCl₃) δ 162.1, 138.4, 134.3, 134.1, 129.1, 128.54, 128.47, 128.4, 128.3, 67.8, 60.8. HRMS (ESI-TOF): Anal. Calcd. For C₁₅H₁₄O₄S+Na⁺: 313.0505, Found: 313.0507. IR (neat, cm⁻¹): υ 3065, 3006, 2943, 2849, 1737, 1448, 1273, 1148.

Example 10

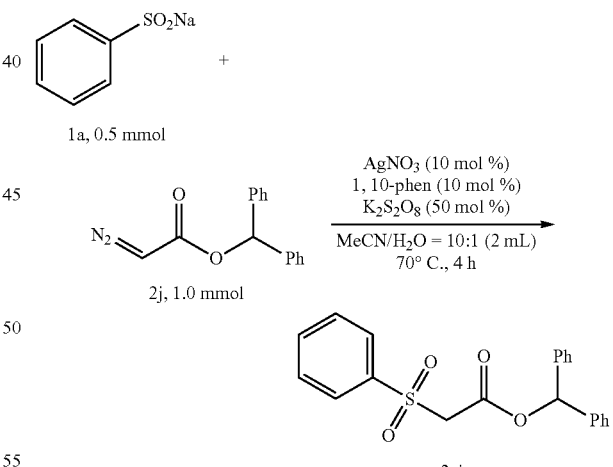

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2j (1.0 mmol, 252.3 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3aj, in a yield 80%. The analytical data of the prepared product are as follows. The data of the actual synthetic products are consistent with the theoretical analysis.

$^1$H NMR (400 MHz, CDCl$_3$) δ 7.76-7.74 (m, 2H), 7.57-7.53 (m, 1H), 7.40-7.36 (m, 2H), 7.32-7.24 (m, 10H), 6.82 (s, 1H), 4.17 (s, 2H). $^{13}$C NMR (100 MHz, CDCl$_3$) δ 161.4, 138.7, 138.2, 134.1, 129.1, 128.4, 128.3, 128.1, 127.1, 78.9, 60.9. HRMS (ESI-TOF): Anal. Calcd. For C$_{21}$H$_{18}$O$_4$S+Na$^+$: 389.0818, Found: 389.0804. IR (neat, cm$^{-1}$): ν 3063, 3007, 2929, 2853, 1738, 1448, 1265, 1149.

Example 11

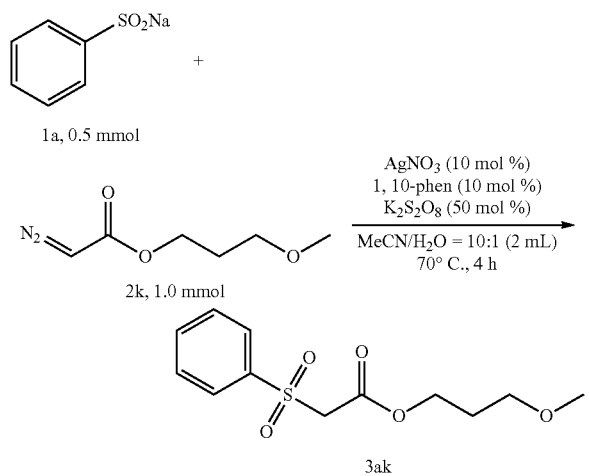

Compound AgNO$_3$ (0.05 mmol, 8.5 mg), 1,10-phen (0.05 mmol, 9.0 mg), K$_2$S$_2$O$_8$ (0.25 mmol, 67.6 mg), 1a (0.5 mmol, 82.1 mg), 2k (1.0 mmol, 158.2 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3ak, in a yield 74%. The analytical data of the prepared product are as follows. The data of the actual synthetic products are consistent with the theoretical analysis.

$^1$H NMR (400 MHz, CDCl$_3$) δ 7.97-7.91 (m, 2H), 7.72-7.68 (m, 1H), 7.61-7.57 (m, 2H), 4.18 (t, J=6.5 Hz, 2H), 4.14 (s, 2H), 3.36 (t, J=6.5 Hz, 1H), 3.30 (s, 3H), 1.85-1.79 (m, 2H). $^{13}$C NMR (100 MHz, CDCl$_3$) δ 162.2, 138.6, 134.2, 129.1, 128.3, 68.4, 63.4, 60.8, 58.5, 28.4. HRMS (ESI-TOF): Anal. Calcd. For C$_{12}$H$_{16}$O$_5$S+Na$^+$: 295.0611, Found: 295.0619. IR (neat, cm$^{-1}$): ν 3065, 2930, 2878, 1737, 1448, 1278, 1151, 1083.

Example 12

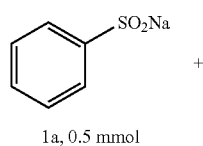

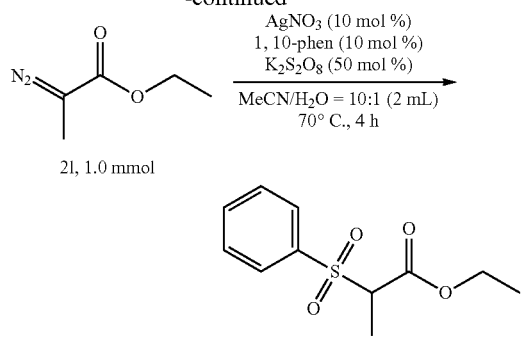

Compound AgNO$_3$ (0.05 mmol, 8.5 mg), 1,10-phen (0.05 mmol, 9.0 mg), K$_2$S$_2$O$_8$ (0.25 mmol, 67.6 mg), 1a (0.5 mmol, 82.1 mg), 2l (1.0 mmol, 128.2 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3al, in a yield 71%. The analytical data of the prepared product are as follows. The data of the actual synthetic products are consistent with the theoretical analysis.

$^1$H NMR (400 MHz, CDCl$_3$) δ 7.91-7.88 (m, 2H), 7.71-7.67 ((m, 1H), 7.60-7.56 (m, 2H), 4.11 (dq, J=0.6, 7.2 Hz, 2H), 4.06 (q, J=7.2 Hz, 1H), 1.58 (d, J=7.2 Hz, 3H), 1.15 (t, J=7.2 Hz, 3H). $^{13}$C NMR (100 MHz, CDCl$_3$) δ 166.1, 136.9, 134.1, 129.2, 128.9, 65.3, 62.1, 13.7, 11.6. HRMS (ESI-TOF): Anal. Calcd. For C$_{11}$H$_{14}$O$_4$S+Na$^+$: 265.0505, Found: 265.0509. IR (neat, cm$^{-1}$): ν 3066, 2985, 2942, 1734, 1448, 1260, 1145, 1083.

Example 13

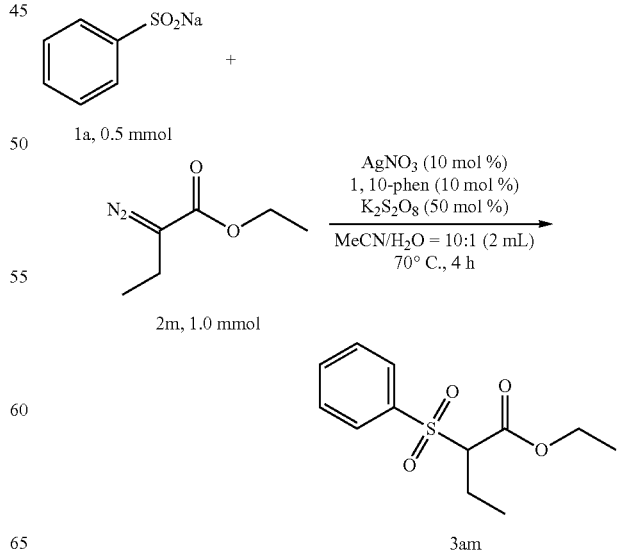

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2m (1.0 mmol, 142.2 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3am, in a yield 66%. The analytical data of the prepared product are as follows. The data of the actual synthetic products are consistent with the theoretical analysis.

¹H NMR (400 MHz, CDCl₃) δ 7.91-7.88 (m, 2H), 7.71-7.67 ((m, 1H), 7.60-7.56 (m, 2H), 4.11 (dq, J=0.6, 7.2 Hz, 2H), 4.06 (q, J=7.2 Hz, 1H), 1.58 (d, J=7.2 Hz, 3H), 1.15 (t, J=7.2 Hz, 3H). ¹³C NMR (100 MHz, CDCl₃) δ 166.1, 136.9, 134.1, 129.2, 128.9, 65.3, 62.1, 13.7, 11.6. HRMS (ESI-TOF): Anal. Calcd. For C₁₂H₁₆O₄S+Na⁺: 279.0662, Found: 279.0669. IR (neat, cm⁻¹): υ 3069, 2979, 2852, 1731, 1451, 1187, 1162, 1079.

Example 14

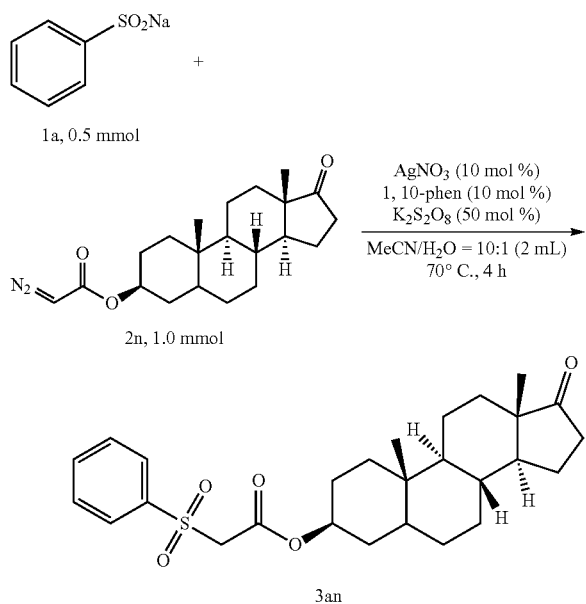

Compound AgNO₃ (0.05 mmol, 8.5 mg), 1,10-phen (0.05 mmol, 9.0 mg), K₂S₂O₈ (0.25 mmol, 67.6 mg), 1a (0.5 mmol, 82.1 mg), 2n (1.0 mmol, 358.5 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3an, in a yield 61%. The analytical data of the prepared product are as follows. The data of the actual synthetic products are consistent with the theoretical analysis.

¹H NMR (400 MHz, CDCl₃) δ 7.96-7.94 (m, 2H), 7.71-7.68 (m, 1H), 7.60-7.57 (m, 2H), 4.71-4.65 (m, 1H), 4.09 (s, 2H), 2.47-2.40 (m, 1H), 2.11-2.01 (m, 1H), 1.92-1.91 (m, 1H), 1.77-1.13 (m, 16H), 0.98-0.94 (m, 1H), 0.85 (s, 3H), 0.82 (s, 3H), 0.71-0.68 (m, 1H). ¹³C NMR (100 MHz, CDCl₃) δ 221.0, 161.7, 138.6, 134.1, 129.0, 128.4, 75.8, 61.1, 54.0, 51.1, 47.6, 44.3, 36.3, 35.7, 35.4, 34.8, 33.3, 31.3, 30.5, 28.0, 26.8, 21.6, 20.3, 13.6, 12.0. HRMS (ESI-TOF): Anal. Calcd. For C₂₇H₃₆O₅S+Na⁺: 495.2176, Found: 495.2160. IR (neat, cm⁻¹): υ 3010, 2928, 2848, 1742, 1448, 1279, 1160, 1086.

Example 15

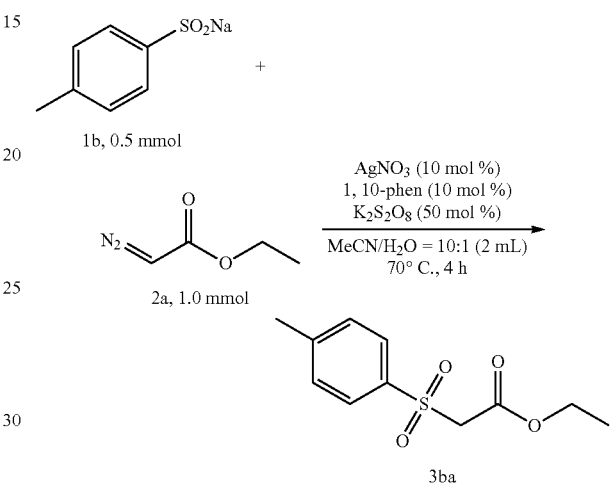

Compound AgNO₃ (0.05 mmol, 8.5 mg), 1,10-phen (0.05 mmol, 9.0 mg), K₂S₂O₈ (0.25 mmol, 67.6 mg), 1b (0.5 mmol, 89.1 mg), 2a (1.0 mmol, 114.1 mg), MeCN/H₂O=10:1 (2.0 mL). The reaction mixture was heated at 70° C. for 4 h, and the reaction was then quenched with saturated Na₂SO₃ solution and the mixture was extracted with ethyl acetate (20 mL×3). The organic layers were combined and dried with anhydrous Na₂SO₄. Removal of the organic solvent followed by flash column chromatographic purification using petroleum and ethyl acetate to obtain β-carbonyl sulfones 3ba, in a yield 63%. The analytical data of the prepared product are as follows. The data of the actual synthetic products are consistent with the theoretical analysis.

¹H NMR (400 MHz, CDCl₃) δ 7.82 (d, J=8.3 Hz, 2H), 7.37 (d, J=8.3 Hz, 2H), 4.15 (q, J=7.1 Hz, 2H), 4.10 (s, 2H), 2.46 (s, 3H), 1.20 (t, J=7.1 Hz, 3H). ¹³C NMR (100 MHz, CDCl³) δ 162.4, 145.3, 135.7, 129.7, 128.5, 62.3, 61.0, 21.6, 13.8. HRMS (ESI-TOF): Anal. Calcd. For C11H14O4S+Na⁺: 265.0505, Found: 265.0515. IR (neat, cm⁻¹): υ 2983, 2929, 2854, 1737, 1400, 1276, 1147, 1084.

Example 16

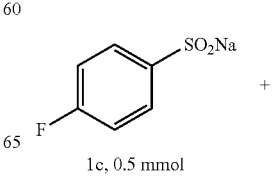

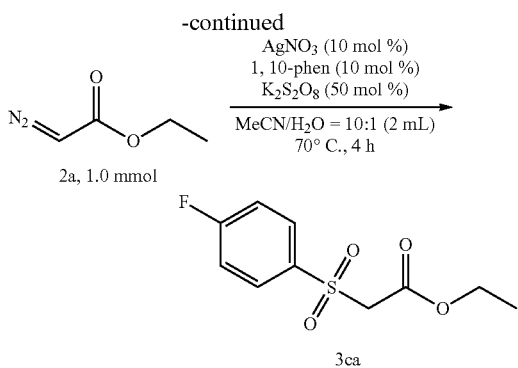

Compound AgNO$_3$ (0.05 mmol, 8.5 mg), 1,10-phen (0.05 mmol, 9.0 mg), K$_2$S$_2$O$_8$ (0.25 mmol, 67.6 mg), 1c (0.5 mmol, 91.1 mg), 2a (1.0 mmol, 114.1 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3ca, in a yield 62%. The analytical data of the prepared product are as follows. The data of the actual synthetic products are consistent with the theoretical analysis.

$^1$H NMR (400 MHz, CDCl$_3$) δ 8.01-7.96 (m, 2H), 7.30-7.24 (m, 2H), 4.18-4.13 (m, 4H), 1.21 (t, J=7.1 Hz, 3H). $^{13}$C NMR (100 MHz, CDCl$_3$) δ 166.0 (d, J=257.2 Hz), 162.2, 134.6 (d, J=3.2 Hz), 131.5 (d, J=9.8 Hz), 116.4 (d, J=22.8 Hz), 62.3, 60.9, 13.8. HRMS (ESI-TOF): Anal. Calcd. For C$_{10}$H$_{11}$FO$_4$S+Na$^+$: 269.0254, Found: 269.0258. IR (neat, cm$^{-1}$): υ 3107, 3073, 2986, 2943, 1736, 1494, 1292, 1147.

Example 17

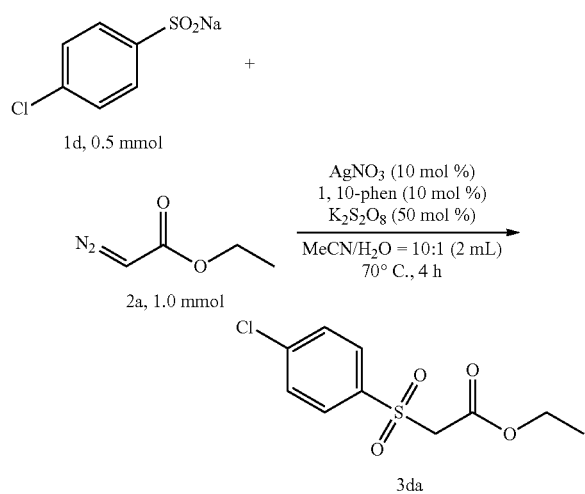

Compound AgNO$_3$ (0.05 mmol, 8.5 mg), 1,10-phen (0.05 mmol, 9.0 mg), K$_2$S$_2$O$_8$ (0.25 mmol, 67.6 mg), 1d (0.5 mmol, 91.1 mg), 2a (1.0 mmol, 114.1 mg), MeCN/H$_2$O=10:1 (2.0 mL). The reaction mixture was heated at 70° C. for 4 h, and the reaction was then quenched with saturated Na$_2$SO$_3$ solution and the mixture was extracted with ethyl acetate (20 mL×3). The organic layers were combined and dried with anhydrous Na$_2$SO$_4$. Removal of the organic solvent followed by flash column chromatographic purification using petroleum and ethyl acetate to obtain β-carbonyl sulfones 3da, in a yield 65%. The analytical data of the prepared product are as follows. The data of the actual synthetic products are consistent with the theoretical analysis.

$^1$H NMR (400 MHz, CDCl$_3$) δ 7.92-7.88 (m, 2H), 7.58-7.55 (m, 2H), 4.18-4.13 (m, 4H), 1.21 (t, J=7.1 Hz, 2H). $^{13}$C NMR (100 MHz, CDCl$_3$) δ 162.1, 140.9, 137.0, 130.0, 129.4, 62.4, 60.7, 13.7. HRMS (ESI-TOF): Anal. Calcd. For C$_{10}$H$_{11}$$^{35}$ClO$_4$S+Na$^+$: 284.9959, Found: 284.9968; Anal. Calcd. For C$_{10}$H$_{11}$$^{37}$ClO$_4$S+Na$^+$: 286.9929, Found: 286.9917. IR (neat, cm$^{-1}$): υ 3093, 2985, 2941, 1736, 1475, 1277, 1151, 1084.

The invention claimed is:

1. A method for preparing a β-carbonyl sulfone, comprising: reacting an α-carbonyldiazo compound with a sodium arylsulfinate, an N,N-bidentate compound as a ligand, a peroxide as an oxidant, in the presence of a metal compound as a catalyst, in a mixed solvent of an organic solvent and water, to obtain the β-carbonyl sulfone,
wherein the α-carbonyldiazo compound has the following chemical formula:

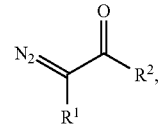

R$^1$ is selected from the group consisting of methyl, ethyl and hydrogen; R$^2$ is alkoxy;
the sodium arylsulfinate has the following chemical formula:

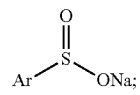

Ar is benzene or substituted benzene;
the β-carbonyl sulfone has the following chemical formula:

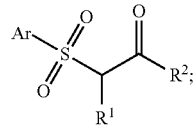

the metal compound is a silver compound or a copper compound;
the peroxide is potassium persulfate, sodium persulfate or ammonium persulfate; and
the N,N-bidentate compound is 1,10-phenanthroline, 2,2'-bipyridine, 4,7-dimethoxy-1,10-phenanthroline, 4,7-diphenyl-1,10-phenanthroline, or 3,8-dibromo-1,10-phenanthroline.

2. The method according to claim 1, wherein the reaction is conducted at 40 to 90° C., for 4 to 12 hours.

3. The method according to claim 1, wherein a molar ratio of the catalyst to the sodium arylsulfinate is 1:10; a molar ratio of the oxidant to the sodium arylsulfinate is from 0.2:1 to 2:1; and a molar ratio of the ligand to the sodium arylsulfinate is 10:1; and a molar ratio of thea-carbonyldiazo compound to the sodium arylsulfinate is 2:1.

4. The method according to claim 1, wherein the reaction is conducted in the air.

5. The method according to claim 1, wherein the organic solvent is acetonitrile.

\* \* \* \* \*